(12) United States Patent
Mi et al.

(10) Patent No.: US 10,716,507 B2
(45) Date of Patent: Jul. 21, 2020

(54) PALPATION ASSISTING APPARATUS, PALPATION ASSISTING SYSTEM, AND PALPATION ASSISTING METHOD

(71) Applicant: FUJITSU LIMITED, Kawasaki-shi, Kanagawa (JP)

(72) Inventors: Xiaoyu Mi, Akashi (JP); Fumihiko Nakazawa, Kawasaki (JP)

(73) Assignee: FUJITSU LIMITED, Kawasaki (JP)

( * ) Notice: Subject to any disclaimer, the term of this patent is extended or adjusted under 35 U.S.C. 154(b) by 858 days.

(21) Appl. No.: 15/231,957

(22) Filed: Aug. 9, 2016

(65) Prior Publication Data

US 2016/0345899 A1 Dec. 1, 2016

Related U.S. Application Data

(63) Continuation of application No. PCT/JP2014/053407, filed on Feb. 14, 2014.

(51) Int. Cl.
*A61B 5/00* (2006.01)
*A61B 5/06* (2006.01)
*A61B 5/11* (2006.01)

(52) U.S. Cl.
CPC .......... *A61B 5/4854* (2013.01); *A61B 5/064* (2013.01); *A61B 5/1127* (2013.01); *A61B 5/1128* (2013.01); *A61B 5/442* (2013.01); *A61B 5/4824* (2013.01); *A61B 5/6826* (2013.01); *A61B 2562/0247* (2013.01)

(58) Field of Classification Search
None
See application file for complete search history.

(56) References Cited

U.S. PATENT DOCUMENTS 5,524,636 A * 6/1996 Sarvazyan ........... A61B 1/0052
600/587
2006/0129068 A1 6/2006 Makosinski et al.
2012/0139828 A1* 6/2012 Lok .......................... G09B 7/00
345/156

(Continued)

FOREIGN PATENT DOCUMENTS

JP 2002-85353 3/2002
JP 2002-536035 10/2002

(Continued)

OTHER PUBLICATIONS

Office Action for Japanese Patent Application No. 2015-562631, dated Mar. 27, 2018.

(Continued)

*Primary Examiner* — Jonathan Cwern
(74) *Attorney, Agent, or Firm* — Staas & Halsey LLP

(57) ABSTRACT

A palpation assisting apparatus includes a synchronization controller configured to synchronize a timing of acquiring pressure data output from a pressure sensor attached to a position in contact with a lesion part with a timing of acquiring positional information of a marker attached to a position corresponding to the pressure sensor, and an entering part configured to store, in a storage part, the pressure data and the positional information of the marker that are acquired at the synchronized timing in association with time information indicating a time at which the pressure data and the positional information are acquired.

11 Claims, 16 Drawing Sheets

(56) References Cited

U.S. PATENT DOCUMENTS

2012/0225413 A1* 9/2012 Kotranza .............. G09B 23/30
434/262

FOREIGN PATENT DOCUMENTS

| JP | 2005-121889 | 5/2005 |
| JP | 2005-227534 | 8/2005 |
| JP | 2005-261546 | 9/2005 |
| JP | 2009-52912 | 3/2009 |
| JP | 2010-274011 | 12/2010 |
| WO | WO 00/44281 | 8/2000 |
| WO | WO 03/063719 A1 | 8/2003 |

OTHER PUBLICATIONS

Patent Abstracts of Japan for JP 2005-227534, published Aug. 25, 2005.
Patent Abstracts of Japan for JP 2005-121889, published May 12, 2005.
Office Action for Japanese Patent Application No. 2015-562631, dated Sep. 25, 2018.
Espacenet Bibliographic Data, Japanese Publication No. 2002-85353, published Mar. 26, 2002.
English Abstract for Japanese Publication No. 2002-536035, published Oct. 29, 2002 from WO 00/44281 A1 published Aug. 3, 2000.
Patent Abstracts of Japan, Publication No. 2009-52912, published Mar. 12, 2009.
Espacenet Bibliographic Data, Japanese Publication No. 2005-261546, published Sep. 29, 2005.
Espacenet Bibliographic Data, Japanese Publication No. 2010-274011, published Dec. 9, 2010.
International Search Report dated Apr. 22, 2014 in corresponding International Application No. PCT/JP2014/053407.
Written Opinion of the International Searching Authority dated Apr. 22, 2014 in corresponding International Application No. PCT/JP2014/053407.
Japanese Office Action dated Aug. 15, 2017 in corresponding Japanese Patent Application No. 2015-562631.

\* cited by examiner

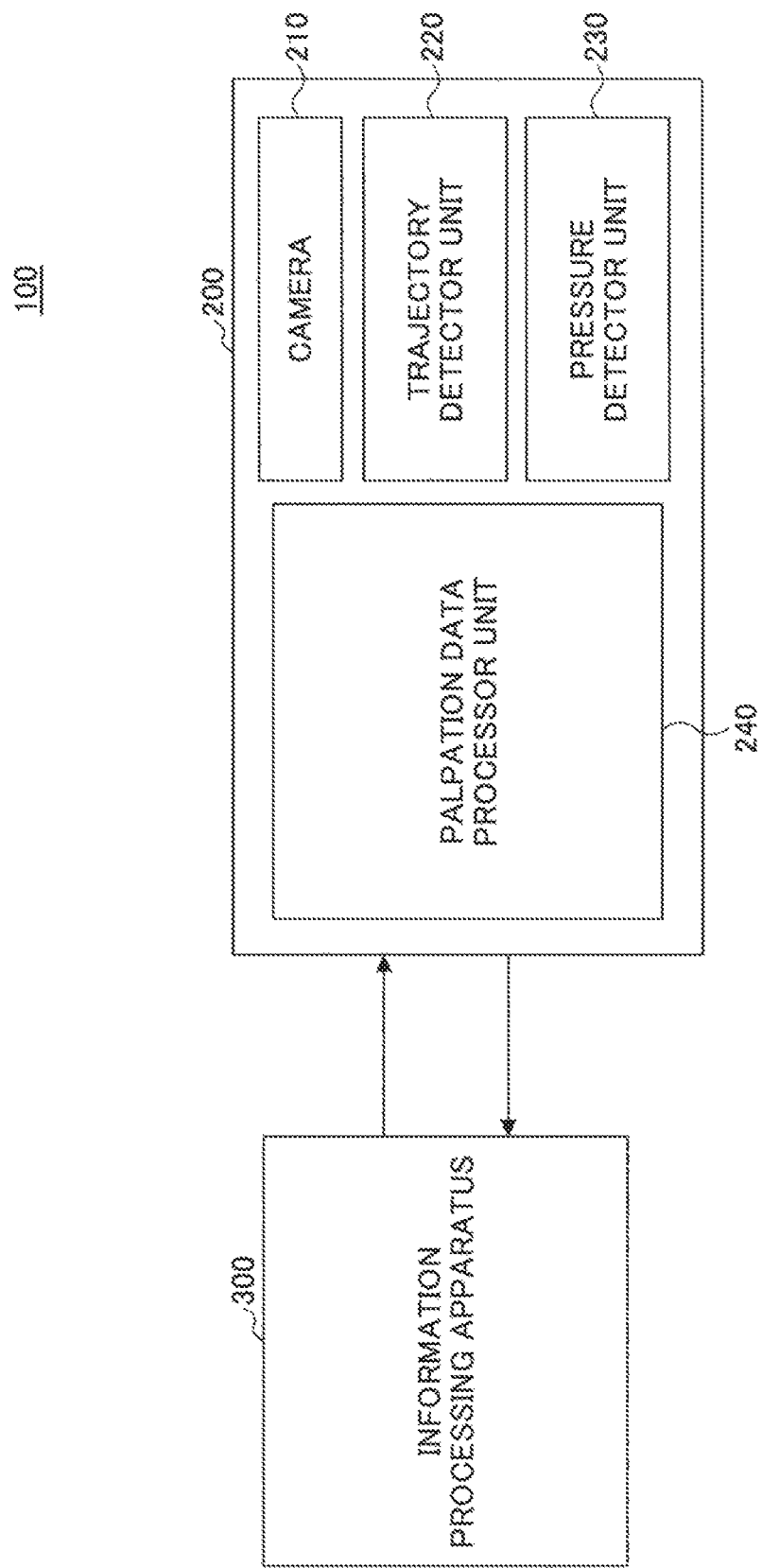

FIG.7

| X COORDINATE | Y COORDINATE | Z COORDINATE | PRESSURE DATA P | ELASTIC MODULUS K | TIME t | CHIEF COMPLAINT |
|---|---|---|---|---|---|---|
| x1 | y1 | z1 | P1 | K1 | t1 | A1 |
| x2 | y2 | z2 | P2 | K2 | t2 | A2 |
| · | · | · | · | · | · | · |
| · | · | · | · | · | · | · |
| · | · | · | · | · | · | · |
| xn | yn | zn | Pn | Kn | tn | An |

| AREA NAME | SCORE | X COORDINATE RANGE | Y COORDINATE RANGE | Z COORDINATE RANGE | PRESSURE DATA P | ELASTIC MODULUS K | CHIEF COMPLAINT |
|---|---|---|---|---|---|---|---|
| AREA 1 | 3 (MEDIUM) | (x1, x2) | (y1, y2) | (z1, z2) | P(min., av., max.) | K(min., av., max.) | A1 |
| . | . | . | . | . | . | . | . |
| . | . | . | . | . | . | . | . |
| . | . | . | . | . | . | . | . |
| AREA n | 4 (SLIGHTLY EXCESS) | (xm, xn) | (ym, yn) | (zm, zn) | P(min., av., max.) | K(min., av., max.) | An |

| ITEM | SCORE | AREA NAME | X COORDINATE RANGE | Y COORDINATE RANGE | Z COORDINATE RANGE | PRESSURE DATA P | ELASTIC MODULUS K | CHIEF COMPLAINT |
|---|---|---|---|---|---|---|---|---|
| ABDOMINAL DISTENSION | 1 | w5 | (x1, x2) | (y1, y2) | (z1, z2) | P1(min., av., max.) | K1(min., av., max.) | A1 |
| WEAKNESS OF LOWER ABDOMINAL PART | 0 | w9 | (x3, x4) | (y3, y4) | (z3, z4) | P2(min., av., max.) | K2(min., av., max.) | A2 |
| · | · | · | · | · | · | · | · | · |
| · | · | · | · | · | · | · | · | · |
| · | · | · | · | · | · | · | · | · |
| TENDERNESS AND RESISTANCE POINT | 1 | wn | (xm, xn) | (ym, yn) | (zm, zn) | Pn(min., av., max.) | Kn(min., av., max.) | An |

320A

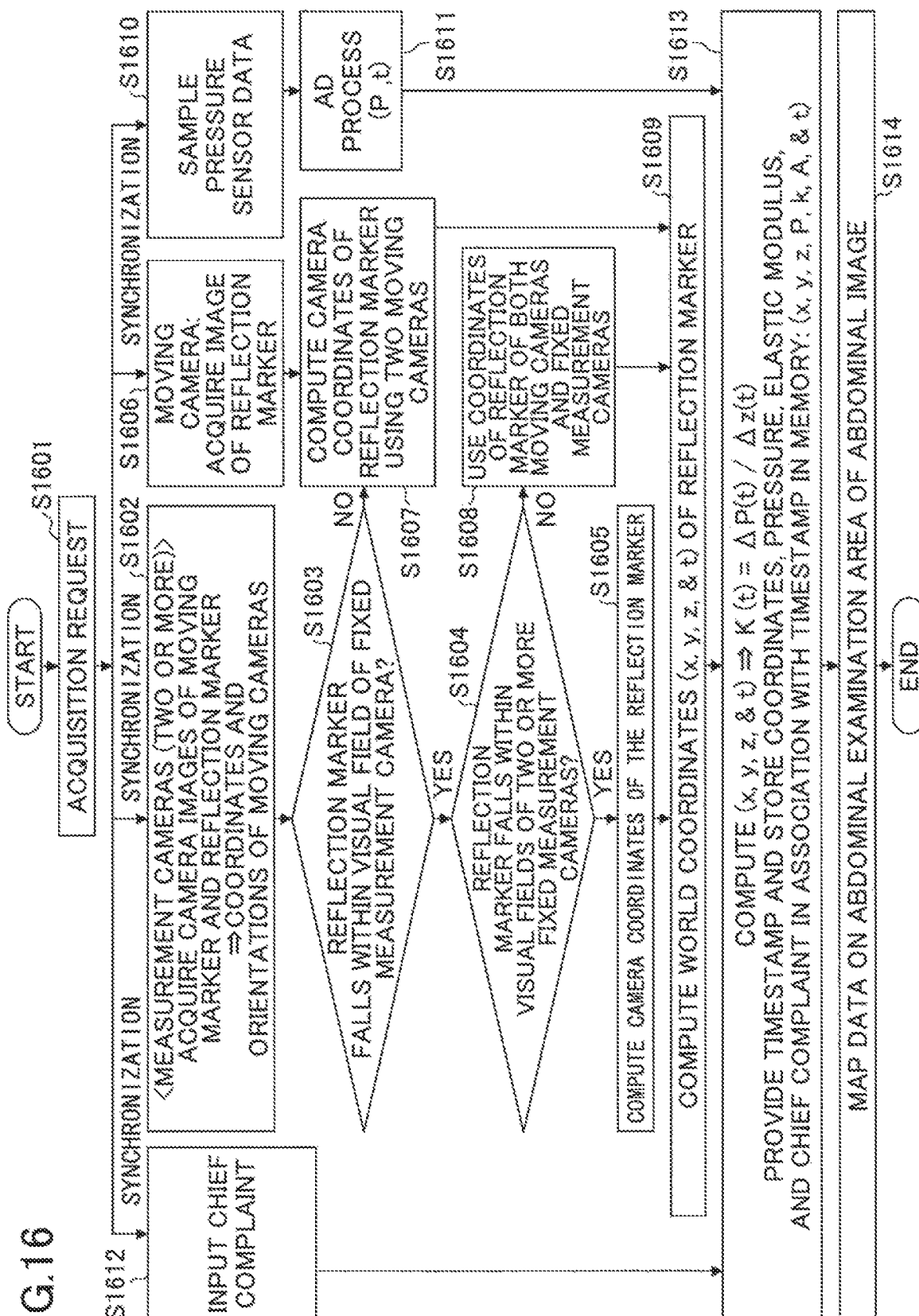

PALPATION ASSISTING APPARATUS, PALPATION ASSISTING SYSTEM, AND PALPATION ASSISTING METHOD

CROSS-REFERENCE TO RELATED APPLICATIONS

This application is a continuation application of International Application PCT/JP2014/053407 filed on Feb. 14, 2014 and designated the U.S., the entire contents of which are incorporated herein by reference.

FIELD

The disclosures discussed herein generally relate to a palpation assisting apparatus, a palpation assisting system, and a palpation assisting method.

BACKGROUND

In traditional oriental medicine including Chinese herbal medicine, there are four basic diagnostic procedures (examinations) used in diagnosing a disease; namely, inspection that observes a patient with eye, listening and smelling examination that hearing voice of the patient, inquiry that asks the patient questions, and palpation that directly touches the patient. The above diagnostic methods are all subjective methods of diagnosing patients based on information on patients acquired through the five physical senses of the palpation examiner, and prescribing appropriate Chinese herbal medicine according to the age and the physical constitution of the patients. Hence, the palpation examiner may need to have vast knowledge and sophisticated skills.

Of these diagnostic methods, diagnostic results obtained by palpation largely rely on a palpation examiner because the palpation examiner obtains biological information of patients by directly touching the patients. A related art technology proposes quantifying the information obtained by the palpation; that is, quantifying the reactive force, namely, abdominal strength, obtained by pressing the abdominal surface of the patient during the palpation of an abdominal part (abdominal examination).

However, the related art technology merely quantifies abdominal strength detected by the palpation (abdominal examination), but may fail to indicate positions of the abdominal part associated with the quantified abdominal strength. That is, the above-described related art technology may fail to relate the process of palpation and detected numerical values. As a result, the diagnostic result of the palpation still remains dependent upon the skills of the palpation examiner.

RELATED ART DOCUMENTS

Patent Documents

Patent Document 1: Japanese Laid-open Patent Publication No. 2005-261546
Patent Document 2: Japanese Laid-open Patent Publication No. 2010-274011

SUMMARY

According to an aspect of an embodiment, there is provided a palpation assisting apparatus that includes a synchronization controller configured to synchronize a timing of acquiring pressure data output from a pressure sensor attached to a position in contact with a lesion part with a timing of acquiring positional information of a marker attached to a position corresponding to the pressure sensor; and an entering part configured to store, in a storage part, the pressure data and the positional information of the marker that are acquired at the synchronized timing in association with time information indicating a time at which the pressure data and the positional information are acquired.

The object and advantages of the invention will be realized and attained by means of the elements and combinations particularly pointed out in the appended claims.

It is to be understood that both the foregoing general description and the following detailed description are exemplary and explanatory and are not restrictive of the invention as claimed.

BRIEF DESCRIPTION OF DRAWINGS

FIG. 1 is a diagram illustrating an example of a system configuration of a palpation assisting system;

FIG. 7 is a diagram illustrating computation of camera coordinates of the reflection marker;

FIG. 11 is a first diagram illustrating an example of a score conversion database;

FIG. 12 is a first diagram illustrating an example of the score conversion database;

FIG. 16 is a flowchart illustrating operations of the palpation assisting system of the second embodiment.

DESCRIPTION OF EMBODIMENTS

Figures 2A, 2B:
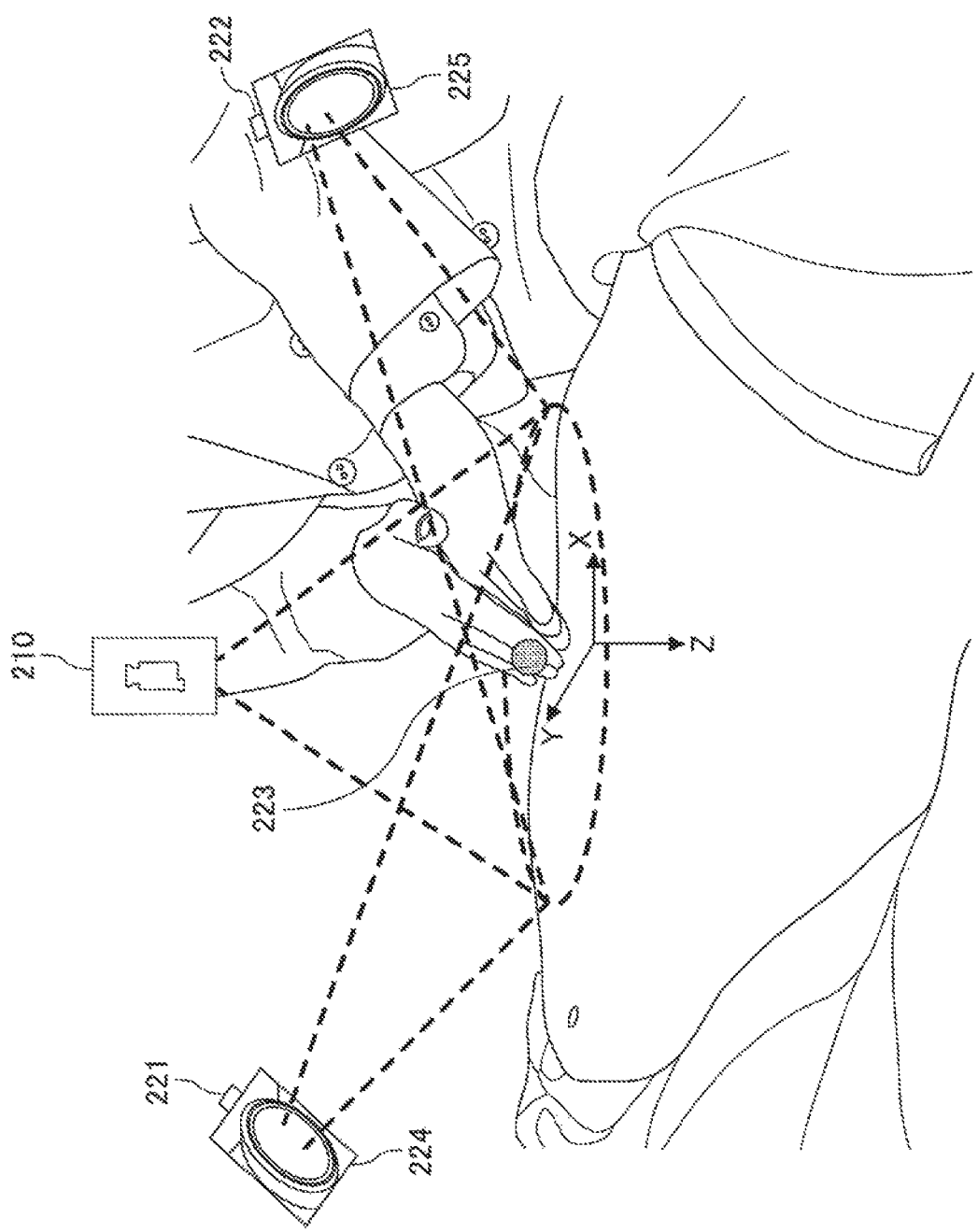
FIGS. 2A and 2B are diagrams illustrating a schematic configuration of the palpation assisting apparatus of a first embodiment.

It may be desirable to provide a palpation assisting system, a palpation assisting apparatus, and a palpation assisting method capable of performing palpation without relying on a palpation examiner.

First Embodiment

The following illustrates a first embodiment with reference to the accompanying drawings. FIG. 1 is a diagram illustrating an example of a system configuration of a palpation assisted system.

The palpation assisting system 100 of the embodiment includes a palpation assisting apparatus 200, and an information processing apparatus 300. In the palpation assisting system 100, the palpation assisting apparatus 200 is configured to provide a palpation result obtained by a palpation examiner palpating a patient as numerically converted palpation result data to the information processing apparatus 300. The information processing apparatus 300 configured to save an analyzed result of the palpation result data as a database.

The palpation assisting apparatus 200 of the embodiment includes a camera 210, a trajectory detector unit 220, a pressure detector unit 230, and a palpation data processor unit 240. The above-described units of the palpation assisting apparatus 200 of the embodiment are connected to one another to serve as one system. Note that the palpation assisting apparatus 200 may further include a sound detector unit.

The palpation assisting apparatus 200 of the first embodiment causes the camera 210 and the trajectory detector unit 220 to detect trajectory of a finger of the palpation examiner, and further causes the pressure detector unit 230 to detect abdominal strength of the abdomen of the patient.

The trajectory of the finger in the embodiment may be indicated by coordinates of the finger of the palpation examiner. The strength of the abdomen in the embodiment is counterforce obtained by the palpation examiner pressing an abdominal surface of the patient.

The palpation assisting apparatus 200 causes the palpation data processor unit 240 to associate the coordinates of the finger of the palpation examiner with the abdominal strength of the patient as synchronized data, and transmit the synchronized data as palpation result data to the information processing apparatus 300.

Next, operations of a palpation assisting apparatus 200 of the embodiment is illustrated with reference to FIGS. 2A and 2B.

FIGS. 2A and 2B are diagrams illustrating a schematic configuration of the palpation assisting apparatus 200 of the first embodiment. FIG. 2A is a diagram illustrating a trajectory detector unit 220, and FIG. 2B is a diagram illustrating a pressure detector unit 230.

The trajectory detector unit 220 of the first embodiment includes near infrared light sources 221 and 222, a reflection marker 223, and measurement cameras 224 and 225.

The near infrared light sources 221 and 222 are configured to apply infrared light to the reflection marker 223. The reflection marker 223 is attached to an area near a finger nail of the hand of the palpation examiner, and is configured to reflect the infrared light applied from the near infrared light sources 221 and 222. The measurement cameras 224 and 225 of the first embodiment is configured to image a position of the reflection marker 223 as the image data.

In the first embodiment, coordinates of an X axis, a Y axis, and a Z axis illustrating the trajectory of the reflection marker 223 are acquired from image data as positional data of the reflection marker 223, and the acquired positional data of the reflection marker 223 are determined as the trajectory of the finger of the palpation examiner.

Note that the near infrared light sources 221 and 222 of the first embodiment may be disposed close to or not close to the measurement cameras 224 and 225. The near infrared light sources 221 and 222 may be fixed in advance to positions capable of applying near infrared light to the reflection marker 223. In this embodiment, the near infrared light is used to detect the trajectory of the finger of the palpation examiner; however, it is not necessary to use the near infrared light to detect the trajectory of the finger of the palpation examiner. For example, infrared light or the like may be used to detect the trajectory of the finger.

In addition, the reflection marker 223 of the first embodiment may have any shape; however, the reflection marker 223 may preferably have a spherical shape.

The trajectory detector unit 220 of the first embodiment includes two measurement cameras 224 and 225; however, the number of the measurement cameras in the trajectory detector unit 220 is not limited to two. The trajectory detector unit 220 may include two or more measurement cameras. The trajectory detector unit 220 may be able to improve detection accuracy of the trajectory of the finger as the trajectory detector unit 220 includes more measurement cameras.

The measurement cameras of the first embodiment may preferably have resolution of 40 million pixels. When the trajectory detector unit 220 of the first embodiment employs a ball marker having a diameter of approximately 6 mm as the reflection marker 223, and three or more measurement cameras each having resolution of 130 million pixels, the trajectory detector unit 220 may be able to detect the position of the fingertip with the accuracy of approximately 0.1 mm.

The pressure detector unit 230 of the first embodiment includes a pressure sensor 231 and a signal processor described later. The signal processor is configured to process signals output from the pressure sensor 231.

The pressure sensor 231 of the first embodiment may be attached to a ball of the finger of the palpation examiner that is in contact with the patient when the palpation examiner examines the patient, and is configured to detect counterforce obtained by the palpation examiner pressing the abdominal surface of the patient, and output the detected counterforce as pressure data. That is, the pressure sensor 231 and the reflection marker 223 are disposed such that the pressure sensor 231 and the reflection marker 223 face each other. In other words, each of the positions of the pressure sensor 231 and the reflection marker 223 is associated with the position of the finger of the palpation examiner.

The pressure sensor 231 of the first embodiment may be formed by using a piezoelectric element or electrostatic capacitance. The pressure sensor 231 of the first embodiment may also be formed by using a pressure gauge element configured to detect a change of the pressure as a change in a resistance value. The pressure sensor 231 of the first embodiment may preferably have resilience analogous to human skin so as not to cause the patient to feel discomfort.

FIG. 2B illustrates an example of one pressure sensor 231 attached to the middle finger of the plant culture system; however, the pressure sensor 231 is not necessarily attached to the middle finger of the palpation examiner. For example, two respective pressure sensors 231 may be attached to the index finger and the annular finger. The pressure sensor 231 may be attached to a palm of the palpation examiner. Moreover, the pressure sensor 231 and the marker may be attached to a glove worn by the hand of the palpation examiner as a method for attaching the pressure sensor 231 to the palpation examiner. In addition, the pressure sensor 231 and the marker may be attached to a robot arm that performs the abdominal examination.

In the first embodiment, an image of a site (e.g., abdominal part) subject to palpation is acquired, and the detected trajectory and pressure are mapped onto the image based on the patient's position or the posture within the image.

Figure 3:
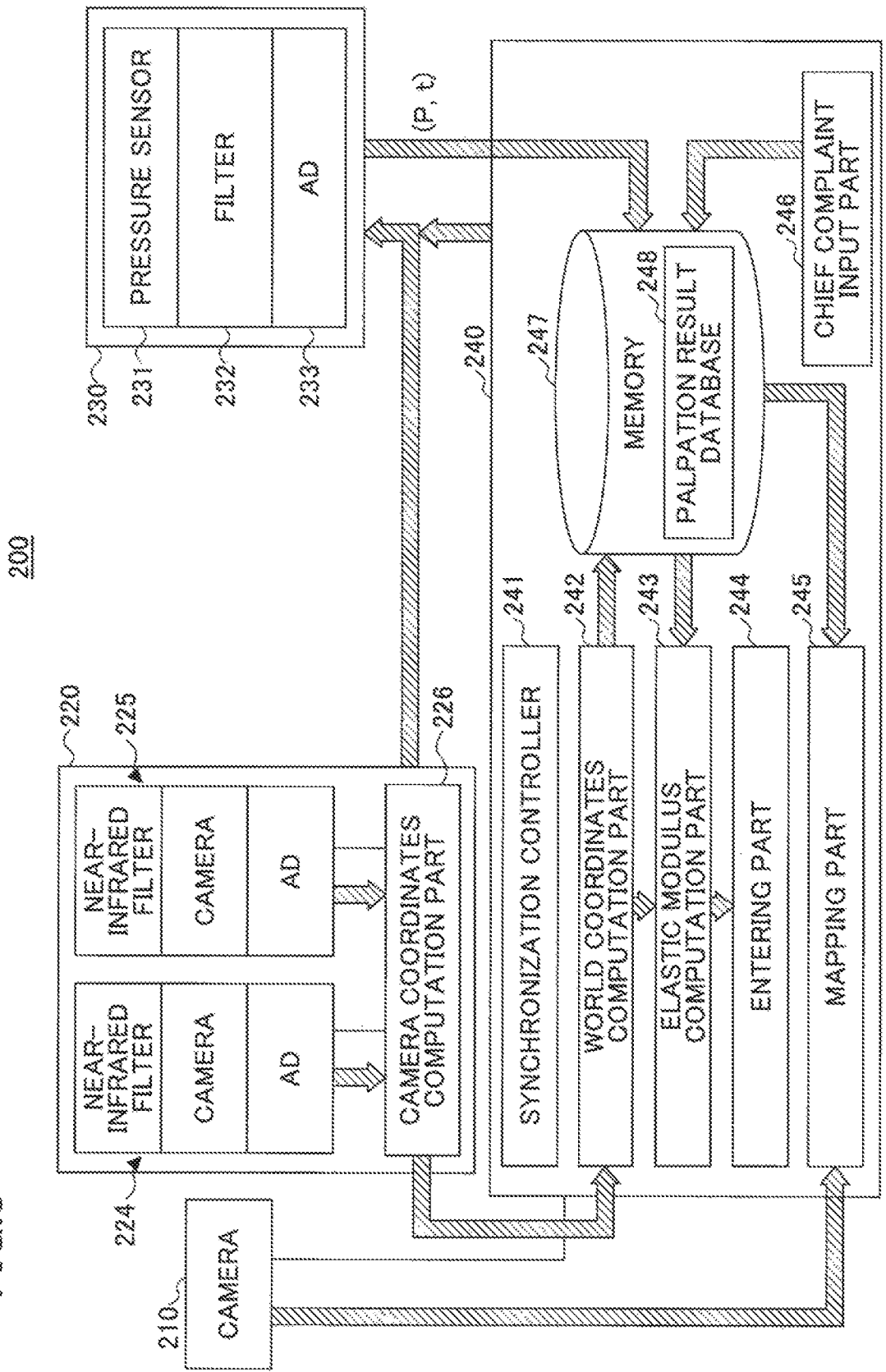
FIG. 3 is a diagram illustrating the functional configuration of the palpation assisting apparatus of the first embodiment.

Next, a functional configuration of the palpation assisting apparatus 200 of the first embodiment is illustrated with reference to FIG. 3. FIG. 3 is a diagram illustrating the functional configuration of the palpation assisting apparatus 200 of the first embodiment.

In the palpation assisting apparatus 200 of the first embodiment, the camera 210 acquires an image of a lesion site of the body of the patient who receives the palpation, and outputs the acquired image to the palpation data processor unit 240.

The trajectory detector unit 220 of the first embodiment includes a camera coordinates computation part 226 connected to the measurement cameras 224 and 225. The camera coordinates computation part 226 of the first embodiment serves as a processor part configured to compute coordinates according to a camera coordinate system (hereinafter called a "camera coordinate system") of the reflection marker 223 in image formed planes of the measurement cameras 224 and 225 based on the image data acquired by the measurement cameras 224 and 225. A predetermined timing of the first embodiment is a timing synchronized with a timing of acquiring the pressure data from the pressure detector unit 230. Derails of the predetermined timing will be described later. Note that the camera coordinates computation part 226 of the embodiment may be disposed in the palpation data processor unit 240.

Note also that each of the measurement cameras 224 and 225 of the first embodiment may include a digital camera, a near infrared film, and an analog-to-digital (AD) converter.

The pressure detector unit 230 of the first embodiment includes a pressure sensor 231, and a filter 232 and an AD converter 233 that serve as a signal processor. Signals output from the pressure sensor 231 are converted into digital signals via the filter 232 and the AD converter 233.

The palpation data processor unit 240 of the first embodiment includes a synchronization controller 241, a world coordinates computation part 242, an elastic modulus computation part 243, an entering part 244, a mapping part 245, a chief complaint input part 246, and a memory 247. The palpation data processor unit 240 of the first embodiment is a computer having a processor and a memory, which when the processor executes a program, may implement processes of components illustrated below.

The synchronization controller 241 of the first embodiment is configured to synchronize a timing of acquiring the camera coordinates from the trajectory detector unit 220 and a timing of acquiring the pressure data from the pressure detector unit 230. That is, the synchronization controller 241 of the first embodiment is configured to transmit a camera coordinates acquisition request to the trajectory detector unit 220 simultaneously with transmitting a pressure data acquisition request to the pressure detector unit 230, and acquire the camera coordinates and the pressure data in association with each other.

In the first embodiment, the trajectory detector unit 220 may receive the camera coordinates acquisition request from the synchronization controller 241 to compute the camera coordinates. Further, the trajectory detector unit 220 of the first embodiment may constantly compute the camera coordinates based on the image data acquired by the measurement cameras 224 and 225, and output the computed camera coordinates to the palpation data processor unit 240 when the trajectory detector unit 220 receives the camera coordinates acquisition request.

The pressure detector unit 230 of the first embodiment may receive the pressure data acquisition request, and output the output signals of the pressure sensor 231 as the pressure data to palpation data processor unit 240, in a manner similar to the trajectory detector unit 220. When the pressure detector unit 230 of the first embodiment constantly acquires the output signals of the pressure sensor 231, and receives the pressure data acquisition request, the pressure detector unit 230 may output the pressure data to the palpation data processor unit 240.

The synchronization controller 241 of the first embodiment is configured to transmit the camera coordinates acquisition request and the pressure data acquisition request at predetermined intervals.

The world coordinates computation part 242 is configured to compute coordinates of the world coordinate system (hereinafter called "world coordinates") based on the camera coordinates computed by the camera coordinates computation part 226. The world coordinates in the first embodiment are coordinates indicating a position of the reflection marker 223 in a coordinate system representing the entire space.

The elastic modulus computation part 243 is configured to compute elastic modulus K (t) based on the pressure data and the world coordinates. The elastic modulus K (t) is a constant coefficient of a primary expression that expresses a relationship between stress and strain, which indicates the firmness of the lesion part. In this embodiment, the elastic modulus K (t) is expressed by the following formula.

$$\text{Elastic modulus } K(t) = \Delta P(t) / \Delta Zw(t)$$

In the above formula, P represents the pressure data, Zw represents a value of a Z axis direction in the world coordinates, and t represents time at which one of the world coordinates and the pressure data are acquired.

When the world coordinates and the elastic modulus are computed, the entering part 244 of the first embodiment stores the world coordinates (Xw, Yw, and Zw) and the pressure data in association with times t at which the world coordinates and the pressure data are acquired into a palpation result database 248 within the memory 247.

The mapping part 245 of the first embodiment is configured to refer to the palpation result database 248, and perform mapping of the pressure data to the lesion site of the patient acquired by the camera 210. The mapping part 245 of the first embodiment may display a mapping result on a not-illustrated display part included in the palpation data processor unit 240.

The chief complaint input part 246 of the first embodiment is configured to receive an input of chief complaint of the patient who currently receives the palpation. The entering part 244 of the first embodiment is configured to store the input chief complaint (text data) in the palpation result database 248 in association with the world coordinates and the pressure data corresponding to a time at which the text data of the chief complaint are input. Derails of the palpation result database 248 of the first embodiment will be described later.

The following illustrates palpation performed by the palpation assisting system 100 of the first embodiment. In the first embodiment, a preprocess of displaying an area subject to palpation on an image of the lesion part imaged by the camera 210 before actual palpation is performed on the lesion part of the patient. Note that the lesion part is hereinafter illustrated as the abdominal part.

Figure 4:
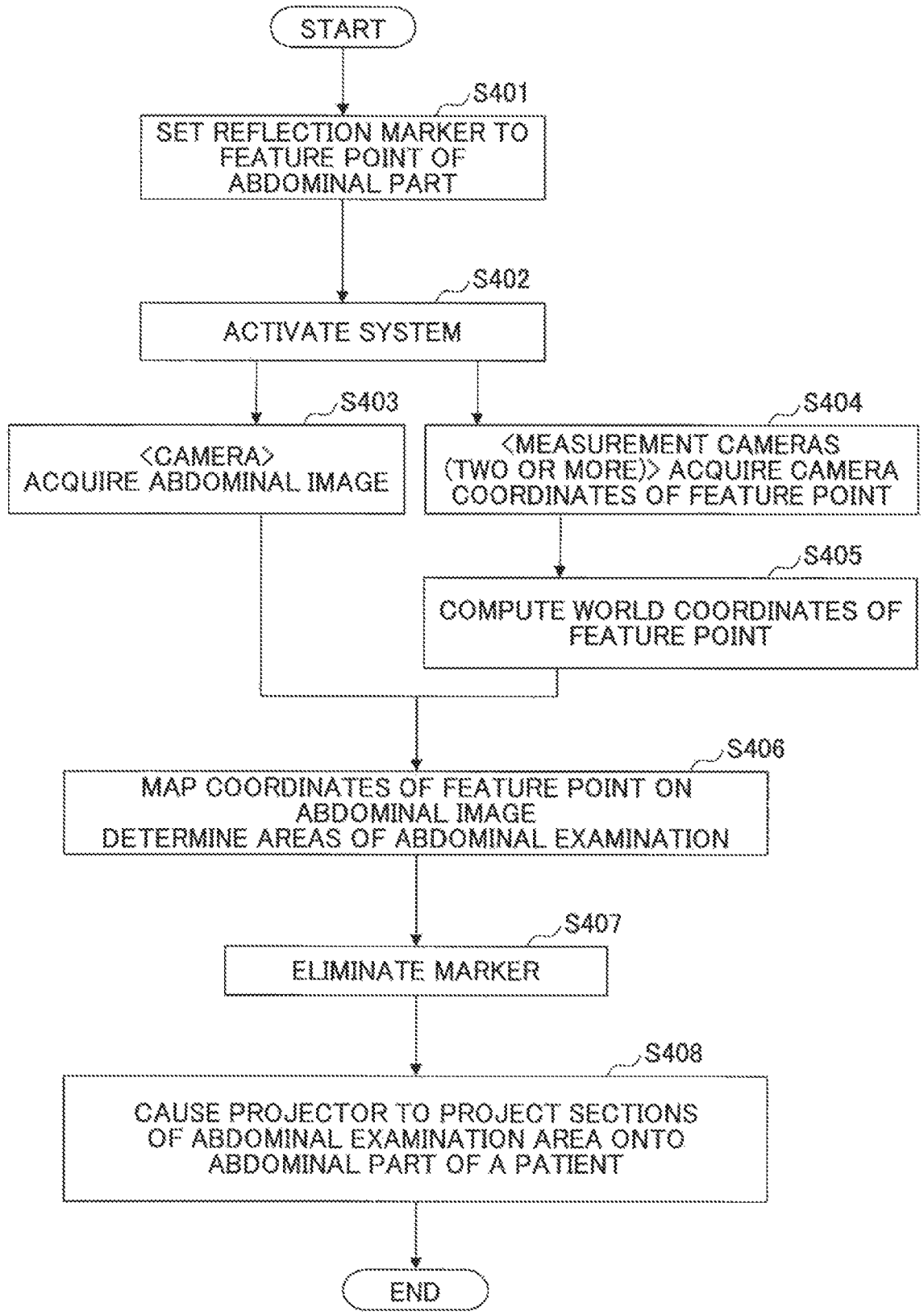
FIG. 4 is a flowchart illustrating a preprocess of palpation using the palpation assisting system.

FIG. 4 is a flowchart illustrating a preprocess of the palpation using the palpation assisting system 100.

The preprocess of the palpation includes setting a reflection marker on a feature point of the abdominal part of the patient by the palpation examiner, for example (step S401). The feature point serves as a reference for determining an area subject to palpation. The reflection marker set in this step may have a form similar to the reflection marker 223 included in the trajectory detector unit 220.

Subsequently, the palpation assisting system 100 of the embodiment is activated (step S402). The camera 210 captures an image of the abdominal part of the patient at the activation of the palpation assisting system 100, and the palpation data processor unit 240 acquires the image of the abdominal part (step S403). Note that when the palpation assisting system 100 is activated, the image may be captured under the control of the palpation data processor unit 240.

The trajectory detector unit 220 acquires camera coordinates of the reflection marker as coordinates of the feature point, and outputs the coordinates of the feature point to the palpation data processor unit 240 (step S404).

When the palpation data processor unit 240 acquires the camera coordinates, the world coordinates computation part 242 computes world coordinates of the feature point based on the camera coordinates (step S405). The mapping part 245 subsequently determines the area subject to palpation by mapping the feature point onto the image of the abdominal part acquired in step S403 (step S406). The marker set in step S401 is subsequently eliminated (step S407).

Subsequently, sections illustrating the area determined in step S406 are projected by a projector or the like onto the abdominal part of the patient (step S408).

In the first embodiment, performing the above-described preprocess enables the palpation examiner to easily identify the area subject to palpation. Note that the process of step S408 may be optionally performed.

Figure 5:
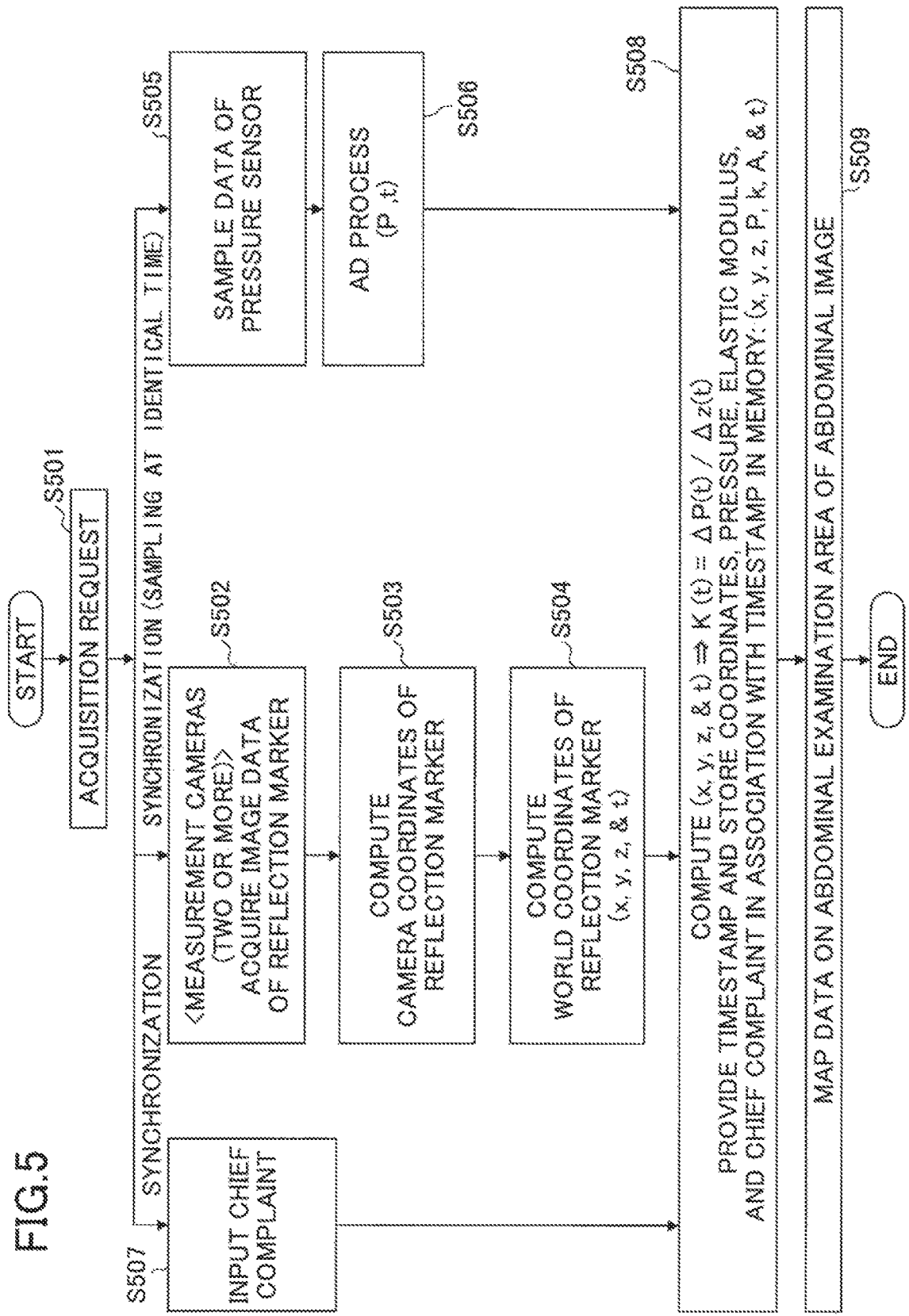
FIG. 5 is a flowchart illustrating operations of the palpation assisting system of the first embodiment.

Next, operations of the palpation assisting system 100 of the first embodiment is illustrated with reference to FIG. 5. FIG. 5 is a flowchart illustrating operations of the palpation assisting system 100 of the first embodiment.

When the palpation examiner starts palpation, the palpation data processor unit 240 causes the synchronization controller 241 to synchronize transmission of a camera coordinate acquisition request to the trajectory detector unit 220 with transmission of a pressure data acquisition request to the pressure detector unit 230 (step S501).

In the palpation assisting apparatus 200 of the first embodiment, when the acquisition requests of step S501 are performed, an acquisition process of the camera coordinates may be performed in parallel with an acquisition process of the pressure data. The acquisition process of the camera coordinates is illustrated.

In the trajectory detector unit 220, the camera coordinates computation part 226 acquires respective image data of the reflection marker 223 imaged by the measurement cameras 224 and 225 upon reception of the camera coordinates acquisition requests (step S502). The camera coordinates computation part 226 subsequently computes the camera coordinates of the reflection marker 223 based on the respective image data (step S503), and outputs the computed camera coordinates to the palpation data processor unit 240. When the palpation data processor unit 240 acquires the camera coordinates, the world coordinates computation part 242 computes world coordinates (x, y, z, and t) based on the camera coordinates (step S504). Details of the world coordinates in the first embodiment will be described later.

Next, the pressure data acquisition process of the first embodiment is described.

The pressure detector unit 230 samples pressure data via the pressure sensor 231 upon reception of the pressure data acquisition request (step S505). The pressure detector unit 230 converts output signals from the pressure sensor 231 into digital pressure data via the filter 232 and the AD converter 233 (step S506), and outputs the digital pressure data to the palpation data processor unit 240.

Note that in this embodiment, when the palpation examiner receives a chief complaint such as pain or discomfort from the patient while performing the palpation, the chief complaint is input into the palpation data processor unit 240 as chief complaint data (step S507). Note that when a specific point corresponding to the pain or discomfort felt by the patient is specified by the abdominal examination data, the process of step S507 may optionally be executed.

The palpation data processor unit 240 subsequently computes an elastic modulus K (t) of the abdominal part based on the world coordinates and the pressure data via the elastic modulus computation part 243. The entering part 244 then provides the associated world coordinates, the pressure data, and the elastic modulus K (t) with time information (timestamp) of transmitting the acquisition requests to the trajectory detector unit 220 and the pressure detector unit 230, then stores the associated world coordinates, the pressure data, and the elastic modulus K (t) with time information (timestamp) in the palpation result database 248 (step S508). Note that the entering part 244 of the first embodiment may store the chief complaint data in association with the world coordinates and the elastic modulus K (t) that are acquired at timing closest to the timing at which the chief complaint is input.

The mapping part 245 subsequently refers to the palpation result database 248, and maps the palpation result data onto the image of the abdominal part acquired by the camera 210 (step S509). The mapping part 245 of the first embodiment may display the marker, for example, at a position at which the elastic modulus K (t) is a predetermined value or more. The mapping part 245 of the first embodiment may perform the mapping to distinguish between the area exhibiting a large elastic modulus K (t) and the area exhibiting a small elastic modulus K (t). The mapping part 245 may perform the mapping of the detected other physical quantity.

In the first embodiment, since the process of palpation is associated with detected numerical values, a physical quantity such as the pressure change or the like on the abdominal part may be detected in real time while pressing the patient's abdominal part.

Figure 6:
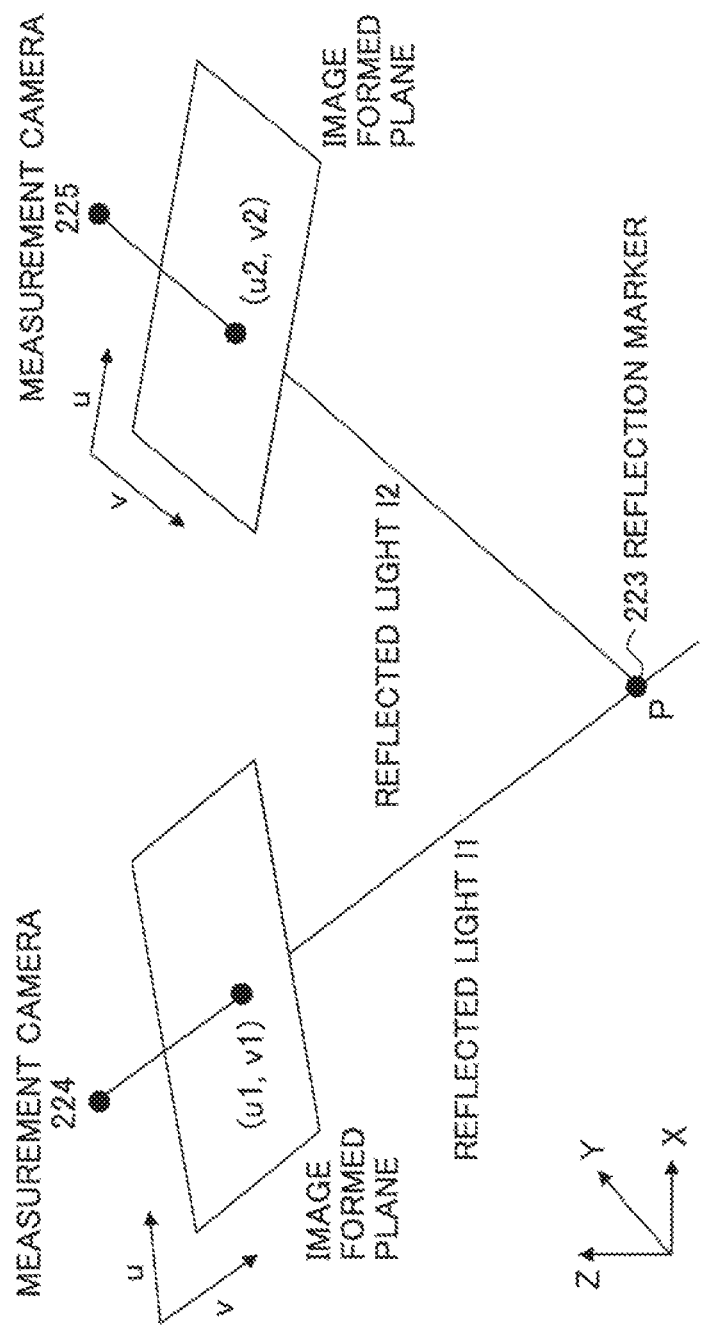
FIG. 6 is a diagram illustrating computation of camera coordinates of a reflection marker.

The following illustrates the computation of the camera coordinates with reference to FIG. 6. FIG. 6 is a diagram illustrating the computation of the camera coordinates of the reflection marker.

The camera coordinates computation part 226 of the first embodiment computes coordinates (u1, v1) of the reflection marker 223 based on a position of the image formed plane of the measurement cameras 224 to which reflection light from the reflection marker 223 is applied. Likewise, the camera coordinates computation part 226 computes coordinates (u2, v2) of the reflection marker 223 based on a position of the image formed plane of the measurement cameras 225 to which reflection light from the reflection marker 223 is applied.

The camera coordinates computation part 226 outputs the two sets of the coordinates as two sets of the camera coordinates to the palpation data processor unit 240.

When the world coordinates computation part 242 acquires the two sets of the camera coordinates, the world coordinates computation part 242 computes world coordinates (Xw, Yw, and Zw) of the reflection marker 223 using a perspective projection matrix $P^1$ and $P^2$ of the measurement cameras 224 and 225.

Note that the perspective projection matrix $P^1$ and $P^2$ may be obtained based on parameters acquired by camera calibration that computes camera characteristics such as lens distortion or focal distances of the measurement cameras 224 and 225.

$$\tilde{m}^1 = P^1 \tilde{X}_w, \quad (1\text{-}1)$$
$$\tilde{m}^2 = P^2 \tilde{X}_w$$

$$\tilde{m}^1 = \begin{bmatrix} u1 \\ v1 \\ 1 \end{bmatrix}, \quad (1\text{-}2)$$

$$\tilde{m}^2 = \begin{bmatrix} u2 \\ v2 \\ 1 \end{bmatrix},$$

$$\tilde{X}_w = \begin{bmatrix} X_w \\ Y_w \\ Z_w \\ 1 \end{bmatrix}$$

$$P^1 = \begin{bmatrix} p^1_{11} & p^1_{12} & p^1_{13} & p^1_{14} \\ p^1_{21} & p^1_{22} & p^1_{23} & p^1_{24} \\ p^1_{31} & p^1_{32} & p^1_{33} & p^1_{34} \end{bmatrix}, \quad (1\text{-}3)$$

$$P^2 = \begin{bmatrix} p^2_{11} & p^2_{12} & p^2_{13} & p^2_{14} \\ p^2_{21} & p^2_{22} & p^2_{23} & p^2_{24} \\ p^2_{31} & p^2_{32} & p^2_{33} & p^2_{34} \end{bmatrix}$$

Next, the palpation result database 248 of the first embodiment is illustrated with reference to FIG. 7. FIG. 7 is a diagram illustrating an example of the palpation result database 248.

The palpation result database 248 of the first embodiment includes X coordinates, Y coordinates, Z coordinates, pressure data, elastic modulus, time, and chief complaint as information items.

In the palpation result database 248, a position indicated by the X coordinates, Y coordinates, and Z coordinates corresponds to a position of the reflection marker 223, that is, a position of the lesion part that is actually touched by a finger of the palpation examiner. In this embodiment, the position indicated by the X coordinate, Y coordinate, and Z coordinate, the pressure data P at the indicated position, the elastic modulus K (t), time t, and the chief complaint of the patient are associated with one another. In the following illustration, values of the X, Y, and Z coordinates and values associated with these coordinates are called "palpation result data".

For example, in FIG. 7, when the palpation examiner presses the position of the world coordinates (x1, y1, and a1) corresponding to the lesion part by the pressure P1 at time t1, the firmness of the pressed part is K1, and the chief complaint of the patient is A1. Note that in this embodiment, the chief complaint A1 indicates that the patient feels resistance when the lesion part is pressed.

In this example, the chief complaint may be classified into three types that are provided with respective symbols, and the symbols may be stored in the palpation result database 248 as the chief complaints of the patient. For example, a chief complaint A0 indicates no chief complaint presented by the patient when the lesion part is pressed, a chief complaint A1 indicates resistance feeling presented by the patient when the lesion part is pressed, and a chief complaint A2 indicates pain presented by the patient when the lesion part is pressed.

In the palpation assisting system 100 of the first embodiment, the information processing apparatus 300 may refer to the palpation result database 248, and provide the palpation result data with scores. Providing the palpation result data with scores may facilitate the palpation examiner's understanding or diagnosis of the patient's conditions.

Figure 8:
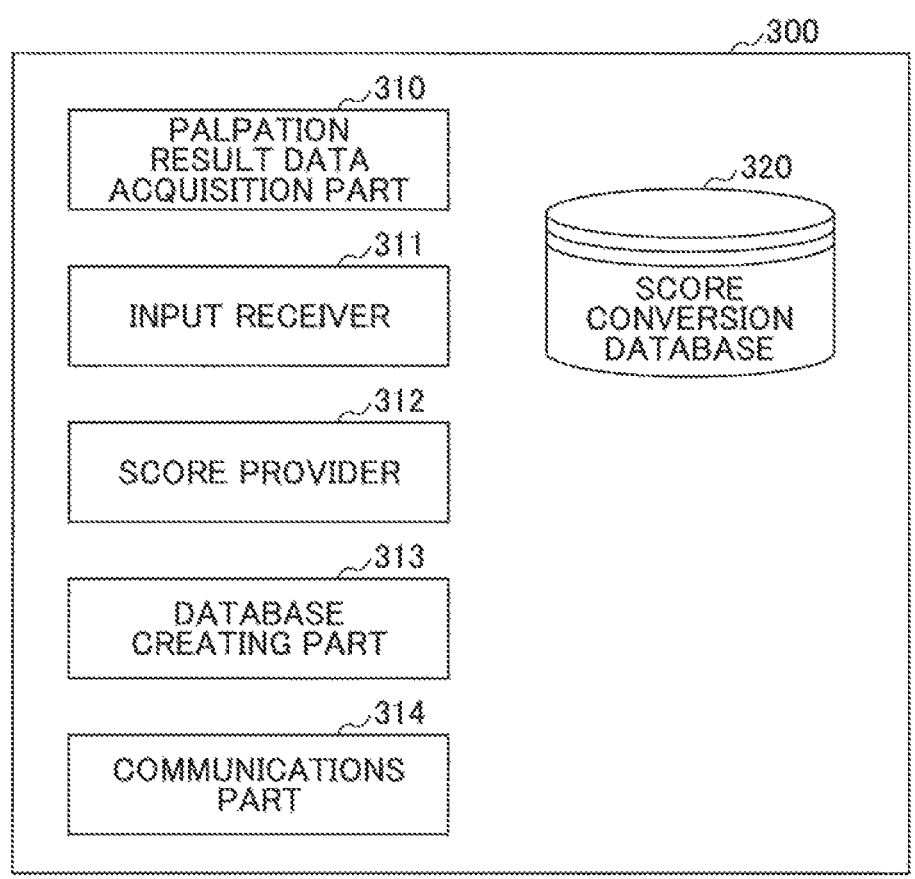
FIG. 8 is a diagram illustrating a functional configuration of an information processing apparatus.

Next, a functional configuration of the information processing apparatus 300 of the first embodiment is illustrated with reference to FIG. 8. FIG. 8 is a diagram illustrating a functional configuration of the information processing apparatus 300.

The information processing apparatus 300 of the first embodiment is a general-purpose computer having a processor device and a storage device, which implements functions of the following components when the processor device executes a program stored in the storage device.

The information processing apparatus 300 includes a palpation result data acquisition part 310, an input receiver 311, a score provider 312, a database creating part 313, and a communications part 314.

The information processing apparatus 300 further includes a score conversion database 320. The score conversion database 320 may be provided in a predetermined storage area within the storage device.

The palpation result data acquisition part 310 is configured to refer to the palpation result database 248, and acquire palpation result data. The input receiver 311 is configured to receive inputs from an input part included in the information processing apparatus 300. More specifically, the input receiver 311 may receive input of a verification result or the like when the palpation examiner verifies the palpation result data.

The score provider 312 is configured to provide scores in accordance with the acquired palpation result data. The database creating part 313 is configured to create a data base of the palpation result data provided with scores. The communications part 314 is configured to perform communications with apparatuses other than the information processing apparatus 300 including the palpation assisting apparatus 200, for example.

Figure 9:
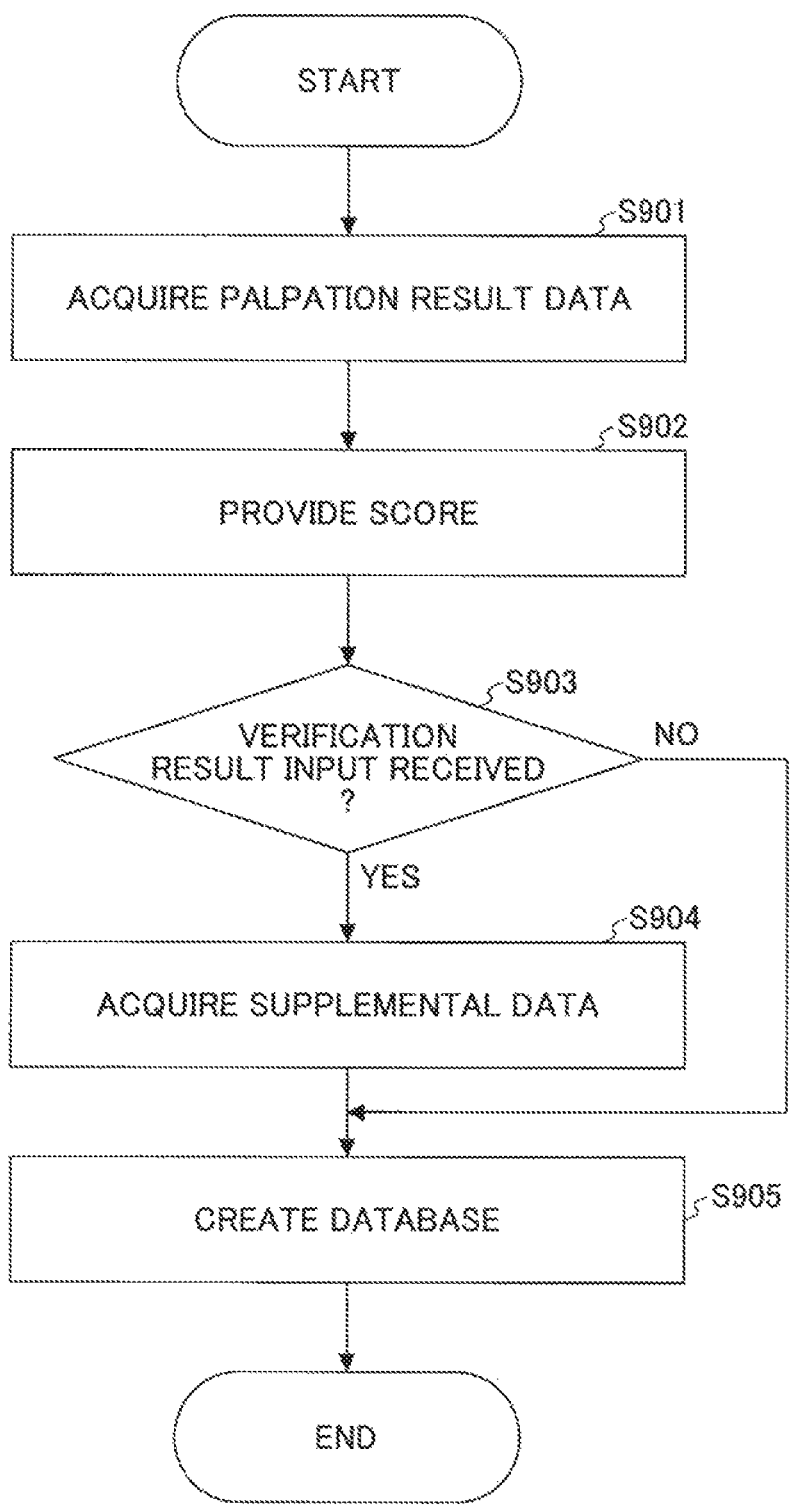
FIG. 9 is a flowchart illustrating operations of the information processing apparatus.

Next, operations of the information processing apparatus 300 of the first embodiment is illustrated with reference to FIG. 9. FIG. 9 is a flowchart illustrating operations of the information processing apparatus 300.

The information processing apparatus 300 of the first embodiment causes the palpation result data acquisition part 310 to acquire palpation result data from the palpation result database 248 (step S901). The information processing apparatus 300 subsequently causes the score provider 312 to provide the palpation result data with scores (step S902). The following illustrates the scores provided to the palpation result data.

In this embodiment, reference values based on which the scores are provided may be set according to items of the patient's conditions. In this example, predetermined thresholds may be set with respect to the pressure data or the elastic modulus in a stepwise manner, and the palpation result data may be provided with scores in accordance with the stepwise thresholds. Further, the palpation result data may be provided with scores indicating the presence or absence of the item of the patient's condition (e.g., a name of the condition of the lesion part.

In addition, thresholds serving as reference values for providing scores may be set by the palpation examiner when the palpation result data are provided with scores.

For example, when the palpation examiner attempts to examine the strain of the abdominal part, thresholds determining strain conditions of the abdominal part are set in the information processing apparatus 300. The score provider 312 may provide the palpation result data with scores based on the set thresholds.

The information processing apparatus 300 may subsequently determines whether the input receiver 311 receives an input of supplementary data as a verification result associated with the scores provided by the palpation examiner or the like (step S903). When the input receiver 311 receives an input of supplementary data, the information processing apparatus 300 acquires the supplementary data, and stores the acquired supplementary data in the score conversion database 320 (step S904). When the input receiver 311 does not receive an input of supplementary data, the information processing apparatus 300 proceeds with later-described step S905.

The database creating part 313 subsequently stores the palpation result data provided with the scores as the score conversion database 320 in the storage device included in the information processing apparatus 300 (step S905).

Figure 10:
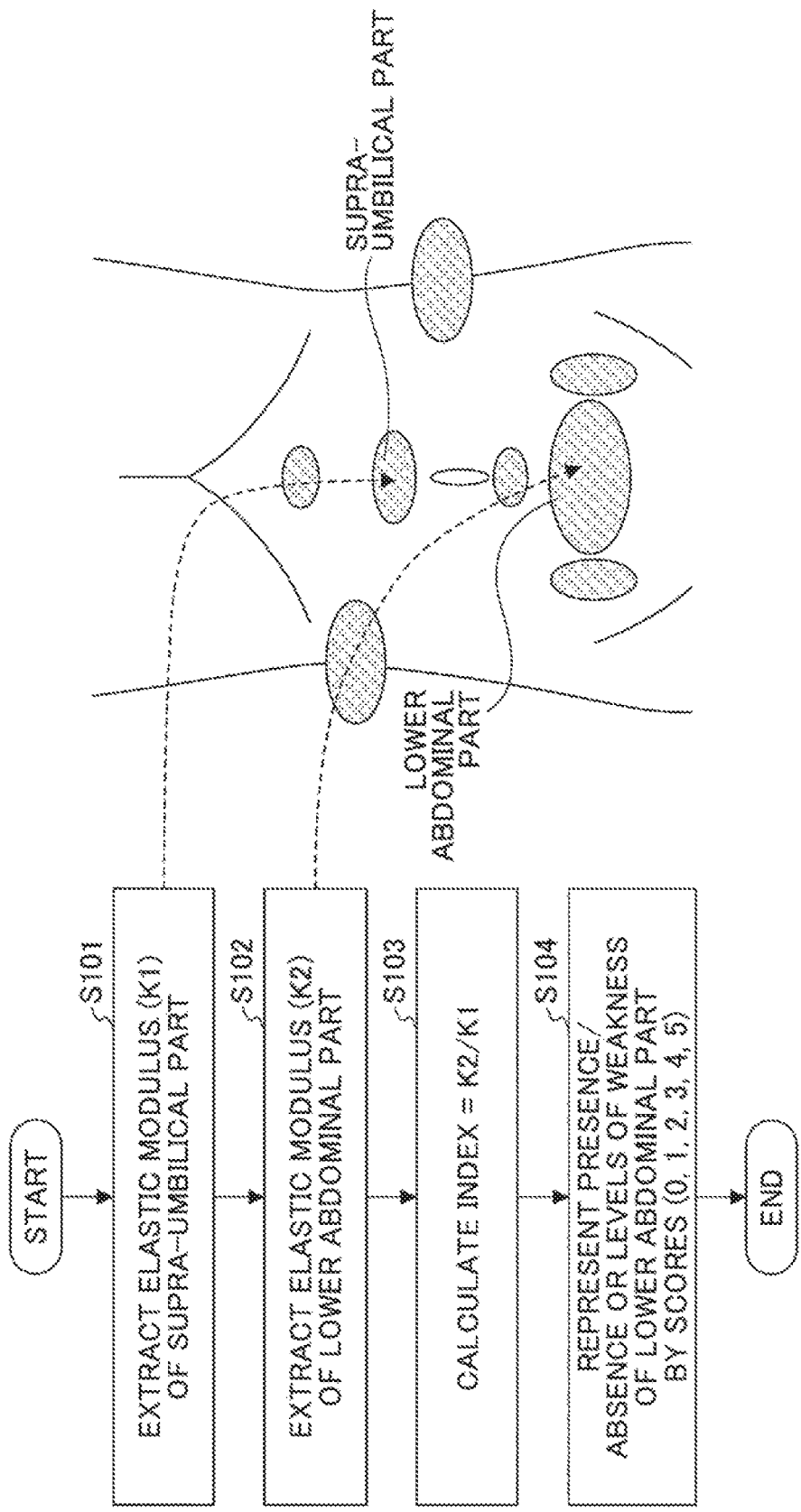
FIG. 10 is a flowchart illustrating a score providing process.

The following illustrates an example of a score providing process according to an embodiment with reference to FIG. 10. FIG. 10 is a flowchart illustrating a score providing process. FIG. 10 specifically illustrates a process of scoring a level of a state called "weakness of a lower abdominal part" in the abdominal part.

The "weakness of a lower abdominal part" indicates softness and weakness of the lower abdominal part in the oriental medicine, where the abdominal walls pressed by a finger may be easily depressed to allow the finger to enter the depressed part. The scoring process illustrated in FIG. 10 provides scores of the presence or absence of the "weakness of the lower abdominal part" or levels of the "weakness of the lower abdominal part", based on an elastic modulus K1 of a supra-umbilical part and an elastic modulus K2 of a lower abdominal part of the lower abdominal part.

In the information processing apparatus 300 of the embodiment, the score provider 312 refers to the X axis, Y axis and Z axis, and extracts an elastic modulus of an area corresponding to a supra-umbilical part in the palpation result data acquired from the palpation result data acquisition part 310 (step S101). The elastic modulus extracted in step S101 is determined as "K1". Subsequently, the score provider 312 extracts an elastic modulus of an area corresponding to a lower abdominal part (step S102). The elastic modulus extracted in step S101 is determined as "K2". In the example of FIG. 10, the information processing apparatus 300 may register coordinates of the areas associated with the supra-umbilical part and the lower abdominal part.

The score provider 312 calculates K2/K1 (step S103). The score provider 312 compares the value calculated in step S103 with a preset threshold, and represents the presence or absence of the weakness of the lower abdominal part, or the level of the weakness of the lower abdominal part as a numerical value (step S104). The score provider 312 of the embodiment may provide a score of 0 as the absent of the weakness of the lower abdominal part when the value of K2/K1 is equal to or greater than a first threshold. Or the score provider 312 of the embodiment may provide any one of scores 1 to 5 as the presence of the weakness of the lower abdominal part when the value of K2/K1 is less than the first threshold.

FIG. 11 is a first diagram illustrating an example of a score conversion database.

The score conversion database 320 illustrated in FIG. 11 indicates an example where levels of the abdominal strength are converted into scores. The score conversion database 320 of FIG. 11 includes an area name, a score, an X coordinate range, a Y coordinate range, a Z coordinate range, pressure P, elastic modulus K, and a chief complaint A as information items.

The area name in the embodiment may be an identifier assigned to an area determined based on the X coordinate range, the Y coordinate range, and the Z coordinate range of the abdomen. The scores in the embodiment may be one of 1 to 5 determined based on thresholds assigned to pressure data P and rigidity (elastic modulus) K in grades. In this embodiment, 1 may be determined as a score less than a minimum one of thresholds of the pressure data P assigned in grades, and the value may be increased as the pressure data P increases.

FIG. 12 is a second diagram illustrating an example of a score conversion database.

The score conversion database 320A illustrated in FIG. 12 is an example of scores converted from the presence or absence of items indicating a specific state of a site receiving the palpation.

The score conversion database 320A includes items illustrating a state, a score, an area name, an X coordinate range, a Y coordinate range, a Z coordinate range, pressure P, elastic modulus K, and a chief complaint A as information items, and the item illustrating the state is associated with other items.

The score conversion database 320A of the embodiment includes a score of 1 or 0, where the score 1 indicates the state of the associated area corresponds to the associated item. For example, the score 1 corresponds to an item "abdominal distension" illustrating a state of distension of an entire abdomen. Hence, the area name w5 determined based on the X coordinate range, the Y coordinate range, and the Z coordinate range corresponds to the state "abdominal distension".

As described above, assigning the score to the palpation result data may easily identify the state of the lesion site objectively.

The pressure sensor 231 of the embodiment illustrated above is designed for, but not limited to, being attached to the middle finger of the palpation examiner. In this embodiment, two or more pressure sensors may be used for palpation.

Figure 13:
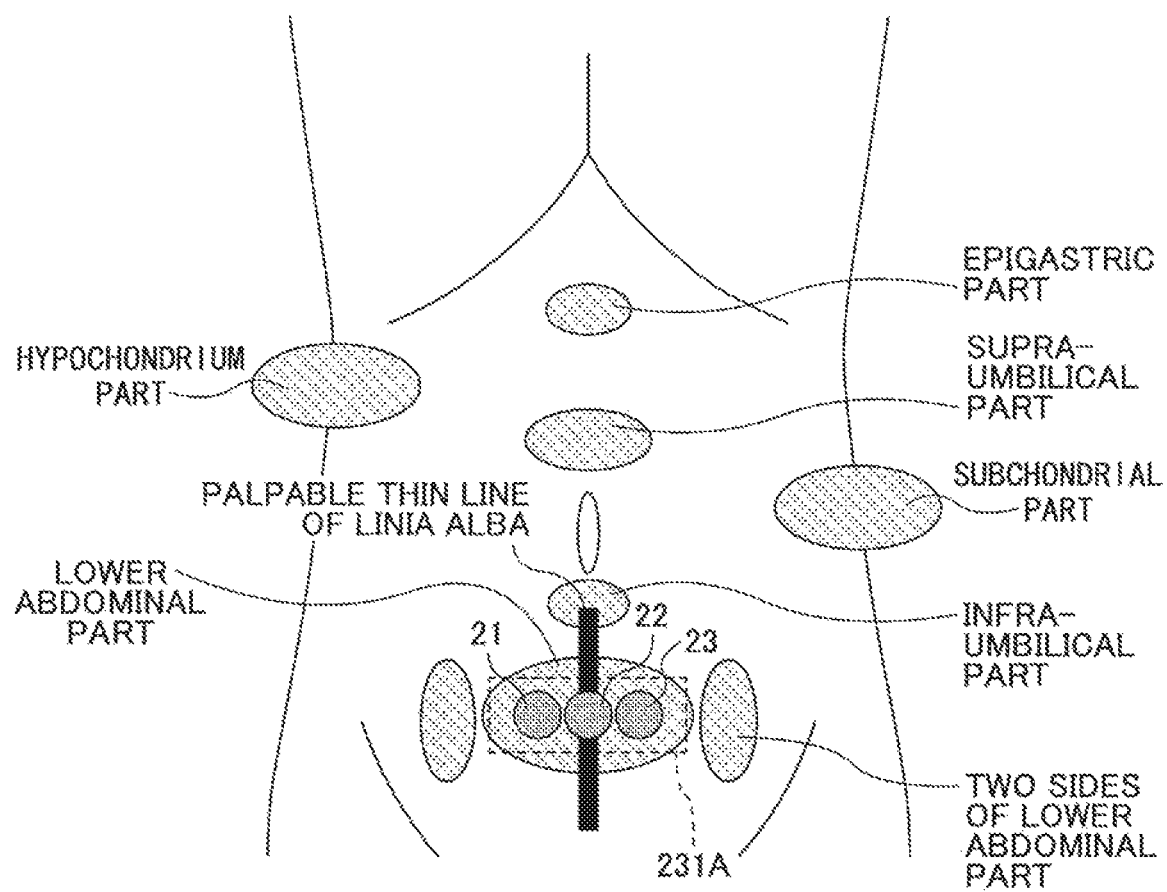
FIG. 13 is a diagram illustrating a modification of the pressure sensor.

FIG. 13 is a diagram illustrating a modification of a pressure sensor.

The pressure sensor 231A illustrated in FIG. 13 includes three pressure sensors 21, 22, and 23. The pressure sensor 21 of the embodiment may be attached to an index finger or an annular finger of the palpation examiner, the pressure sensor 22 may be attached to a middle finger of the palpation examiner, and the pressure sensor 23 may be attached to the annular finger or the index finger.

The palpation assisting apparatus 200 of the embodiment may store palpation result data associated with the pressure sensors 21, 22, and 23 in a palpation result database 248.

The information processing apparatus 300 of the embodiment may assign a score using a compared result of an elastic modulus Ka computed based on the pressure data P of the pressure sensor 22 and an elastic modulus Kb computed based on the pressure data P of the pressure sensor 23.

For example, when the elastic modulus Ka is greater than the elastic modulus Kb by a predetermined value or more, the score provider 312 may assign a score indicating the area corresponding to an item of "palpable thin line of linia alba". The "palpable thin line of linia alba" indicates a state in which a chord such as a pencil lead is present under the skin of the middle of the abdominal wall.

In the first embodiment illustrated above, the coordinates of the fingertip of the palpation examiner who has performed palpation that are synchronized with the pressure data detected at the coordinates of the fingertip may be acquired in real time. Further, resilience (elastic modulus) at the pressed part may be computed based on the acquired pressure data and fingertip coordinates. Moreover, pulsation of palpitation appearing in the lesion part may be detected by the pressure sensor. In addition, information including the depressed amount of the finger and the place of the palpitation when the palpitation has appeared may be acquired in real time as the pressure data and the coordinates.

Accordingly, the palpation may be quantified (numerically converted), and the palpation may be performed without relying on the palpation examiner as a result.

Second Embodiment

The following illustrates a second embodiment with reference to the accompanying drawings. The second embodiment differs from the first embodiment in that, the number of measurement cameras is increased, and the measurement cameras are configured to move along visual lines of the palpation examiner. Accordingly, the following illustration of the second embodiment merely includes the difference between the first embodiment and the second embodiment. The functional configurations similar to those of the first embodiment are provided with the same reference numbers, and duplicated illustration is omitted from the specification.

Figure 14:
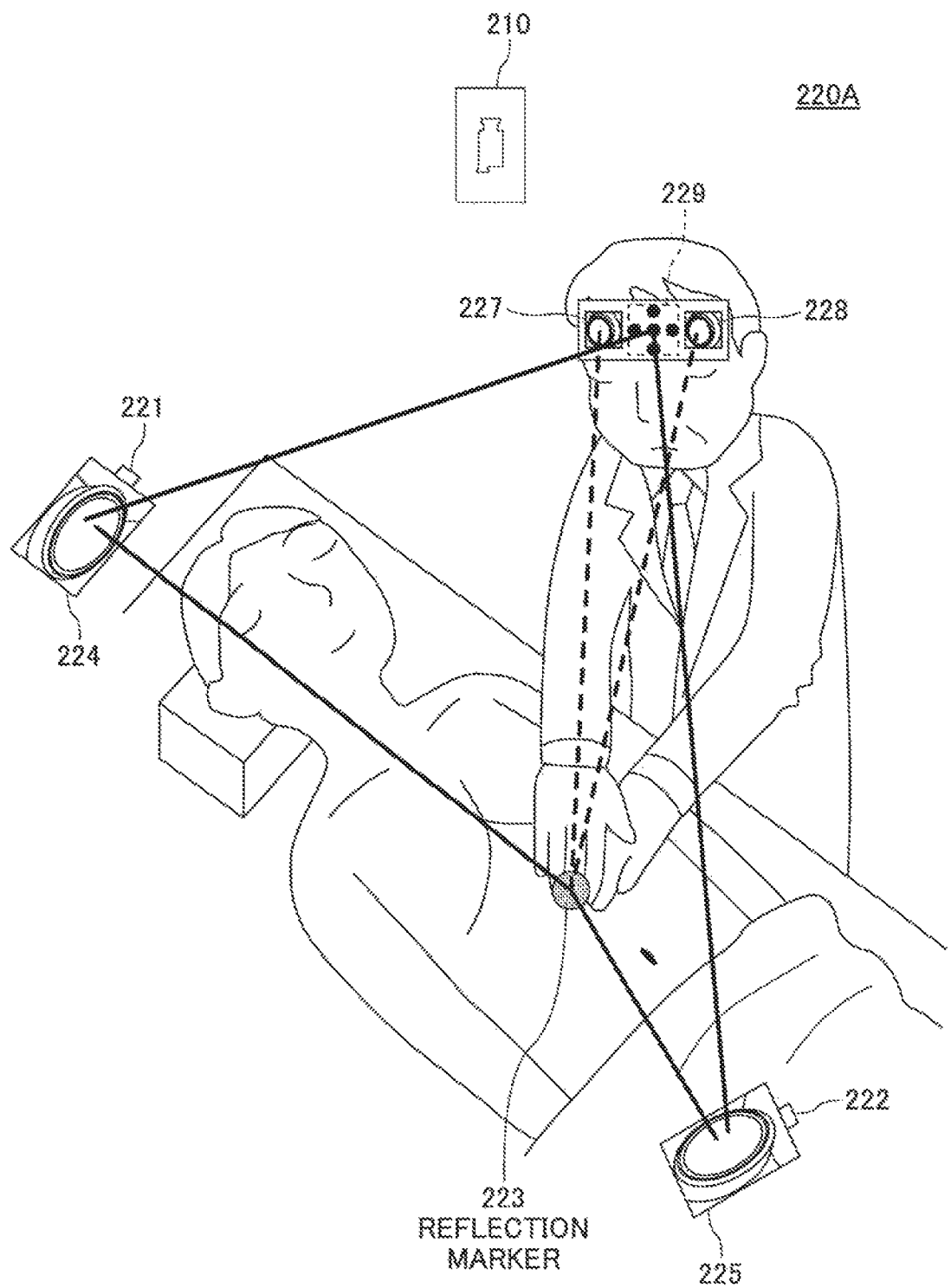
FIG. 14 is a first diagram illustrating a schematic configuration of a palpation assisting apparatus of a second embodiment.

FIG. 14 is a first diagram illustrating a schematic configuration of a palpation assisting apparatus of the second embodiment.

A trajectory detector unit 220A of the second embodiment includes measurement cameras 227 and 228 attached to the forehead of the palpation examiner, and a reflection marker 229. In the following illustration, the measurement cameras 227 and 228 attached to the forehead of the palpation examiner are called moving cameras 227 and 228.

In the trajectory detector unit 220A of the second embodiment, positions of the moving cameras 227 and 228, and the posture of the palpation examiner are specified by reflection light of the near infrared light applied to the reflection marker 229, and the fixed measurement cameras 224 and 225. In the second embodiment, world coordinates of a reflection marker 223 are computed based on an image of the reflection marker 223 imaged by at least two of the measurement cameras 224 and 225, and the moving cameras 227 and 228. This indicates that even when the reflection marker 223 is not imaged by the fixed measurement cameras 224 and 225, the moving cameras 227 and 228 may be able to detect the position of the reflection marker 223 in the second embodiment.

Alternatively, the reflection marker 229 may be disposed between the moving cameras 227 and 228 in the second embodiment. The reflection marker 229 of the second embodiment may have any shape; however, the reflection marker 229 may be preferably have a cruciate shape.

Moreover, the near infrared light source 221 and 222 of the second embodiment may preferably be disposed at positions from which each of the near infrared light sources 221 and 222 applies near infrared light on both the reflection marker 223 and the reflection marker 229.

In the second embodiment, the moving cameras 227 and 228 configured to image the reflection marker 223 worn by the finger of the palpation examiner are attached to the forehead of the palpation examiner, which may be able to eliminate a dead angle formed at the time of imaging the reflection marker 223 by the measurement cameras.

Note that the number of the moving cameras is two in the example of FIG. 14; however, the number of the moving cameras is not limited to two. For example, the number of moving cameras may be one.

Figure 15:
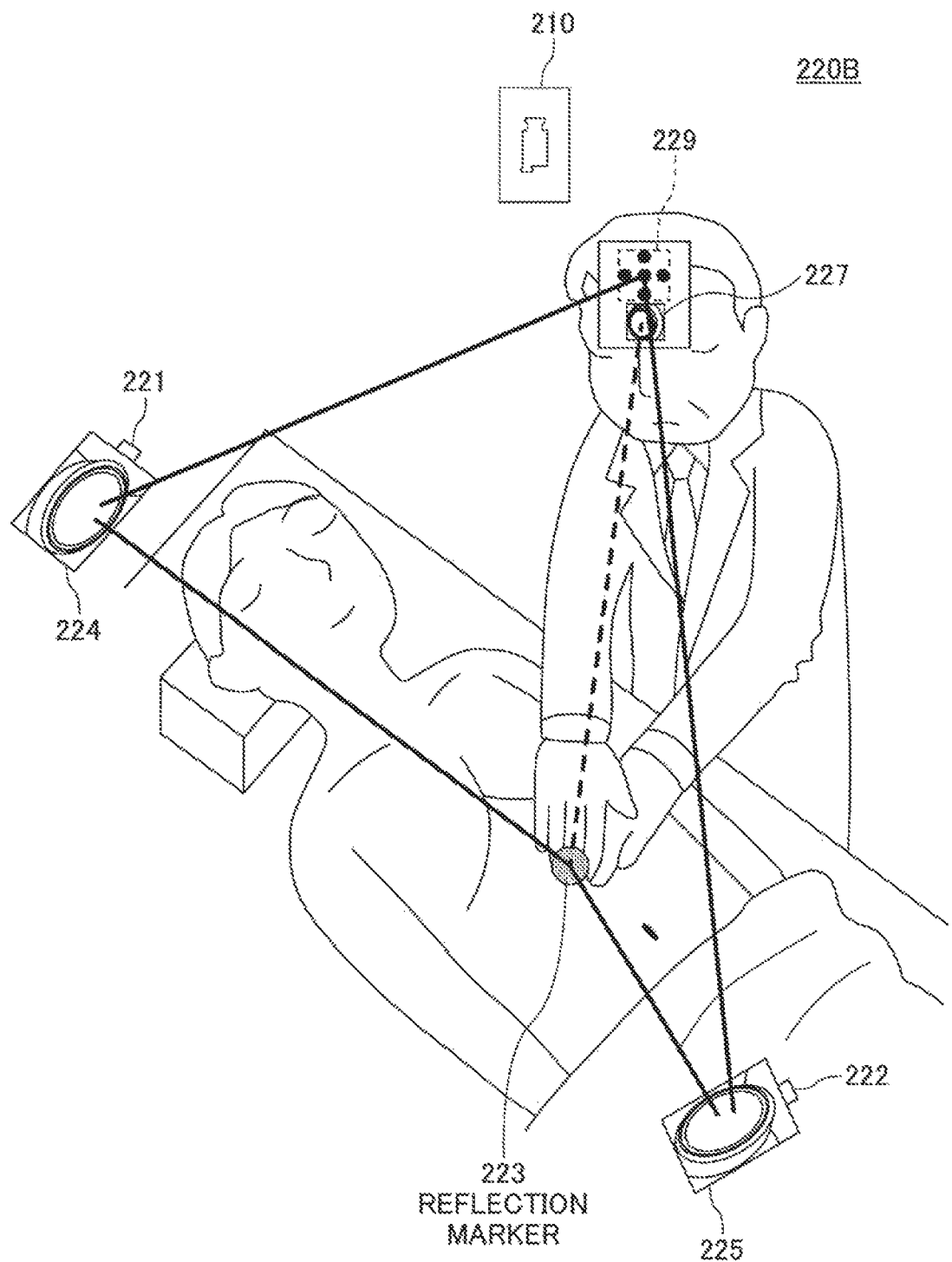
FIG. 15 is a second diagram illustrating a schematic configuration of the palpation assisting apparatus of the second embodiment.

FIG. 15 is a second diagram illustrating a schematic configuration of a palpation assisting apparatus of the second embodiment.

FIG. 15 illustrates an example of a trajectory detector unit 220B in which the number of moving cameras attached to the forehead of the palpation examiner is only one (i.e., the moving camera 227).

In this embodiment, the fixed measurement cameras 224 and 225 are configured to identify the position of the moving camera 227 and the posture of the palpation examiner. Further, the coordinates of the reflection marker 223 may be detected when the reflection marker 223 is imaged by any two of the three measurement cameras 224 and 225, and the moving camera 227.

Next, operations of the palpation assisting system 100 of the second embodiment is illustrated with reference to FIG. 16. FIG. 16 is a flowchart illustrating operations of the palpation assisting system 100 of the second embodiment.

Note that the flowchart illustrated in FIG. 16 illustrates operations of both the trajectory detector units 220A and 220B. Hence, the following illustration is based on the operations of the palpation assisting system 200 that includes the trajectory detector unit 220A.

When the palpation examiner starts palpation, the palpation data processor unit 240 causes the synchronization controller 241 to synchronize transmission of a camera coordinate acquisition request to the trajectory detector unit 220A with transmission of a pressure data acquisition request to the pressure detector unit 230 (step S1601).

The camera coordinates computation part 226 of the second embodiment acquires camera coordinates of the reflection marker 223 based on the image acquired by the measurement cameras 224 and 225 in a manner similar to the first embodiment when the reflection marker 223 falls within the visual fields of the two measurement cameras 224 and 225. Further, the camera coordinates computation part 226 of the second embodiment acquires the camera coordinates of the reflection marker 223 based on an image acquired by the moving cameras 227 and 228 when the reflection marker 223 falls outside the visual fields of the two measurement cameras 224 and 225. In addition, the camera coordinates computation part 226 of the second embodiment acquires the camera coordinates of the reflection marker 223 using one of the moving cameras 227 and 228 when the reflection marker 223 falls within one of the visual fields of the measurement cameras 224 and 225.

The following illustrates a camera coordinates computation process.

In the trajectory detector unit 220A, the camera coordinates computation part 226 causes the measurement cameras 224 and 225 to acquire images of the reflection marker 223 and the reflection marker 229 to identify positions (coordinates) and orientations of the moving cameras 227 and 228 attached to the palpation examiner (step S1602). The camera coordinates computation part 226 subsequently determines whether the reflection marker 223 falls within one of the visual fields of the measurement cameras 227 and 228 based on the images acquired by the moving cameras 227 and 228 (step S1603). In step S1603, when the reflection marker 223 falls within neither of the visual fields of the measurement cameras 227 and 228, the camera coordinates computation part 226 processes step S1607 described later.

In step S1603, when the reflection marker 223 falls within one of the visual fields of the measurement cameras 227 and 228, the camera coordinates computation part 226 determines whether the reflection marker 223 falls within both the visual fields of the measurement cameras 227 and 228 (step S1604). In step S1604, when the reflection marker 223 falls within only one of the visual fields of the measurement cameras 227 and 228, the camera coordinates computation part 226 processes step S1608 described later.

When the reflection marker 223 falls within both the visual fields of the measurement cameras 227 and 228 in step S1604, the camera coordinates computation part 226 computes the camera coordinates of the reflection marker 223 based on the images of the measurement cameras 227 and 228 (step S1605), and processes step S1609 described later. The process of step S1605 is similar to the process of step S503 illustrated in FIG. 5, and a duplicated illustration is thus omitted from the specification.

In the trajectory detector unit 220A, the camera coordinates computation part 226 causes the moving cameras 227 and 228 to acquire images of the reflection marker 223 (step S1606) Note that the process of step S1606 is performed in synchronization with the process of step S1605.

The camera coordinates computation part 226 subsequently computes two sets of camera coordinates of the reflection marker 223 in the two moving cameras 227 and 228 based on the images acquired in step S1606 (step S1607), and then proceeds with later-described step S1609.

That is, in step S1607, the camera coordinates of the reflection marker 223 may be obtained by the two moving cameras 227 and 228 when the reflection marker 223 is present neither of visual fields of the measurement cameras 224 and 225. Thus, in the second embodiment, the camera coordinates may be obtained even if the reflection marker 223 is positioned in respective blind angles of the measurement cameras 224 and 225.

Further, when the reflection marker 223 is present in one of the moving cameras 227 and 228 in step S1608, the camera coordinates computation part 226 computes the camera coordinates of the reflection marker 223 by using one of the moving cameras 227 and 228 (step S1608). That is, the camera coordinates computation part 226 utilizes one of the moving cameras 227 and 228 in combination with the moving cameras 227 and 228.

The processes from step S1609 to step S1614 of FIG. 16 are similar to those from step S504 to step S509 of FIG. 5, and a duplicated description is thus omitted from the specification.

According to the second embodiment, even if the reflection marker 223 is present in the blind angles of the fixed measurement cameras 224 and 225, the camera coordinates of the reflection marker 223 may be acquired by the moving cameras. Hence, according to the second embodiment, the palpation may be performed in a wide area of the lesion part without concern for the blind angles of the measurement cameras 224 and 225, and the palpation result may be quantified.

According to the embodiments, the palpation may be performed without relying on the palpation examiner.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority or inferiority of the invention. Although the embodiments of the present invention have been described in detail, it should be understood that the various changes, substitutions, and alterations could be made hereto without departing from the spirit and scope of the invention.

What is claimed is:

1. A palpation data processing apparatus configured to be coupled to a pressure sensor and a marker, the palpation data processing apparatus comprising:
   a memory;
   an input part; and
   a processor coupled to the memory and the input part, the processor configured to perform a process including
      while the palpation data processing apparatus is coupled to the pressure sensor and the marker, while the pressure sensor is attached to a first portion on a palpation examiner who palpates a lesion part, and while the marker is attached to a second portion on the palpation examiner, synchronizing a timing of acquiring pressure data output from the pressure sensor with a timing of acquiring positional information of the marker;
   storing, in the memory, the pressure data and the positional information of the marker that are acquired at the synchronized timing in association with time information indicating a time at which the pressure data and the positional information are acquired; and
   upon receiving an input of chief complaint data through the input part of a patient receiving palpation, storing the chief complaint data in association with time information indicating time of the input and the positional information of the marker in the memory.

2. The palpation data processing apparatus as claimed in claim 1, wherein the palpation data processing apparatus is further configured to be coupled to measurement cameras, and wherein the process further includes, while the palpation data processing apparatus is coupled to the pressure sensor, the marker, and the measurement cameras,
   capturing images by the measurement cameras,
   computing coordinates of the marker in a world coordinates system based on the positional information of the marker acquired from the images captured by the measurement cameras, the images captured by the measurement cameras are used to measure a position of the marker, and
   the storing stores in the memory the pressure data and the coordinates of the world coordinates system in association with the time information.

3. The palpation data processing apparatus as claimed in claim 2, wherein the process further includes
   computing elastic modulus of the lesion part based on the pressure data, the coordinates of the world coordinates system, and the time information, and
   wherein the storing stores in the memory the elastic modulus in association with the pressure data, the coordinates of the world coordinates system, and the time information.

4. The palpation data processing apparatus as claimed in claim 3, wherein the process further includes
   acquiring an image of a lesion part by a lesion part imaging camera configured to image the lesion part; and
   displaying, on a display part, distribution of the pressure data corresponding to the positional information of the marker onto the acquired image of the lesion part.

5. The palpation data processing apparatus as claimed in claim 4, wherein
the measurement cameras include at least two or more measurement cameras that are fixed to predetermined positions.

6. The palpation data processing apparatus as claimed in claim 2, wherein the palpation data processing apparatus is further configured to be coupled to moving cameras, and wherein the process further includes, while the palpation data processing apparatus is coupled to the pressure sensor, the marker, the measurement cameras, and the moving cameras,
capturing images by the moving cameras, and
computing of the coordinates computes the coordinates of the world coordinates system based on the positional information of the marker in the images captured by the moving cameras, the moving cameras to move in accordance with movement of the marker.

7. The palpation data processing apparatus as claimed in claim 6, wherein
the computing of the coordinates computes the coordinates of the world coordinates system based on the positional information of the marker in the images of the marker captured by the measurement cameras and the images of the marker captured by the moving cameras that move in accordance with the movement of the marker.

8. The palpation data processing apparatus as claimed in claim 1, wherein the positional information of the marker indicates local coordinates of the marker in an image represented by a camera coordinates system.

9. The palpation data processing apparatus as claimed in claim 1, wherein the storing stores the chief complaint data in association with the pressure data and the positional information that are acquired at a time closest to the time the chief complaint is input, from among multiple sets of the time information stored in the memory.

10. A palpation data processing method executed by a computer, the palpation data processing method comprising:
while a pressure sensor is attached to a first portion on a palpation examiner who palpates a lesion part and while a marker is attached to a second portion on the palpation examiner, synchronizing a timing of acquiring pressure data output from the pressure sensor with a timing of acquiring positional information of the marker;
storing, in a memory, the pressure data and the positional information of the marker that are acquired at the synchronized timing in association with time information indicating a time at which the pressure data and the positional information are acquired; and
upon receiving an input of chief complaint data of a patient receiving palpation, storing the chief complaint data in association with time information indicating time of the input and the positional information of the marker in the memory.

11. A palpation data processing system comprising:
a pressure sensor to be attached to a first portion on a palpation examiner who palpates a lesion part;
a marker to be attached to a second portion on the palpation examiner; and
a palpation data processing apparatus configured to assist palpation based on pressure data output from the pressure sensor and positional information of the marker,
wherein the palpation data processing apparatus includes
a memory; and
a processor coupled to the memory and configured to perform a process including
synchronizing a timing of acquiring the pressure data with a timing of acquiring the positional information of the marker,
storing, in a memory, the pressure data and the positional information of the marker that are acquired at the synchronized timing in association with time information indicating a time at which the pressure data and the positional information are acquired; and
upon receiving an input of chief complaint data of a patient receiving palpation, storing the chief complaint data in association with time information indicating time of the input and the positional information of the marker in the memory.

* * * * *